US00PP13476P2

(12) United States Plant Patent
Bradford

(10) Patent No.: US PP13,476 P2
(45) Date of Patent: Jan. 14, 2003

(54) PLUM TREE NAMED 'YUMMYROSA'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/014,035

(22) Filed: Dec. 13, 2001

(51) Int. Cl.[7] ..... A01H 5/00
(52) U.S. Cl. ..... Plt./184; Plt./185
(58) Field of Search ..... Plt./184, 185

(56) References Cited

U.S. PATENT DOCUMENTS

PP3,617 P 9/1974 Anderson ..... Plt./184
PP7,503 P 4/1991 Bradford ..... Plt./184

*Primary Examiner*—Bruce R. Campell
*Assistant Examiner*—W C Haas

(57) ABSTRACT

The present invention relates to a plum tree, *Prunus salicina*, and more particularly to a new and distinct variety broadly characterized by a large size, vigorous, hardy, self-fertile, productive and regular bearing tree. The fruit matures under the ecological conditions described approximately the last week in June, with first picking on Jun. 24, 2001. The fruit is uniformly medium in size, excellent in flavor, globose in shape, clingstone in type, firm in texture, yellow to red in flesh color, and dark red in skin color. The variety was developed as a an open pollinated seedling of an unnamed plum possessing red skin and red flesh.

1 Drawing Sheet

BOTANICAL CLASSIFICATION

*Prunus salicina.*

BACKGROUND OF THE VARIETY

In a continuing effort to improve the quality of shipping fruits, I, the inventor, typically hybridize a large number of peach, nectarine, plum, apricot, and cherry seedlings each year. In an effort to exhibit recessive traits, I also grow a lesser number of open pollinated seeds of each of these fruits. In my breeding grounds during the summer of 1993 I gathered open pollinated seeds from several different unpatented plum trees which bore red fruit. One particular group of these seeds was collected from an open pollinated seedling of 'Black Beaut' (U.S. Plant Pat. No. 3,617) that produced large red plums having red flesh and tart flavor. This group of seeds, designated as "19P442 (OP)", was germinated and grown as a seedlings on their own root in my greenhouse, and transplanted to a cultivated area of my experimental orchard at Bradford Farms near Le Grand, Calif. in Merced County (San Joaquin Valley).

The present invention relates to a new and distinct variety of plum tree, which has been denominated varietally as 'YUMMYROSA'. It was selected by me during the 1998 fruiting season as a single plant from the group of open pollinated seedlings described above. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is similar to its grandparent, 'Black Beaut' (U.S. Plant Pat. No. 3,617), by producing dark red plums that are firm in texture, globose in shape, and that mature in June, but is distinguished therefrom and an improvement thereon by being self-fertile, by producing an abundance of pollen, by being much more productive, and by producing fruit that is sweeter in flavor and matures about two weeks later.

The present variety is most similar to 'Purple Majesty' (U.S. Plant Pat. No. 7,503), by producing dark red plums that are firm in texture, and that mature about the third week in June, but is distinguished therefrom and an improvement thereon by being self-fertile, by producing an abundance of pollen, by being more productive, and by producing fruit that is red in flesh color toward the skin, juicier, and sweeter in flavor.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin County), Calif., and was developed at the state of firm ripe on Jun. 27, 2001, on the original tree during its eighth growing season. All major color code designations are by reference to the Inter-Society Color Council, National Bureau of Standards. Common color names are also used occasionally.

Tree

Size: Large, reaching and maintaining a height of 13' [3.96 m.] after eight growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.
Form: Trained to a central leader system by pruning.
Hardiness: Hardy with respect to central California winters.
Heat tolerance: Observed to perform adequately in typical central California climatic conditions, which typically include prolonged periods of heat.
Drought tolerance: Variety is developed for commercial orchards and requires regular irrigation.
Production: Very productive, thinning necessary.
Fertility: Self-fertile.
Bearing: Regular bearer with no alternate bearing yet observed.
Trunk:
*Size.*—Medium, reaching a maximum diameter of 4" [102 mm.] after the eighth growing season.
*Texture.*—Shaggy.
*Bark color.*—Dark grayish yellowish brown [81. d.gy.yBr].
*Lenticels.*—Average in number. Color: Brownish orange [54. brO]. Average Size: ¼" [6.4.].
Branches:
*Size.*—Diameter of first scaffold is 1¾" [45 mm.] measured 12 inches from the central leader, typical of *Prunus salicina*, and dependent upon cultural practices and climatic conditions.
*Texture.*—Smooth on 1st year wood, increasing roughness with age.
*Color.*—1st Year wood Topside: Moderate reddish brown [43. m.rBr]. 1st Year Wood Underside: Moderate yellow green [120. m.YG]. Older Wood: Deep brown [56. deep Br].
*Lenticels.*—Numerous, small. Color: Deep orange [51. deep O]. Average size: 1/16" [1.6 m.].
Leaves:
*Size.*—Small. Average Length: 2⅝" [67 mm.]. Average width: 1⅛" [29 mm.].
*Arrangement.*—Alternate.
*Thickness.*—Medium.
*Form.*—Elliptical.
*Apex.*—Acuminate.
*Base.*—Acute with an average angle of seventy degrees.
*Surface.*—Smooth.
*Color.*—Dorsal Surface: Dark olive green [126. d.OlG]. Ventral Surface: Moderate olive green [125. m.OlG].
*Margin.*—Finely serrate.
*Venation.*—Pinnately net veined.
*Petiole.*—Average Length: 7/16" [11.1 mm.]. Average Thickness: 3/64" [1.2 mm.]. Color: Moderate yellow green [120. m.YG] with a Moderate reddish brown [43. m.rBr] tinge on the topside.
*Stipules.*—Number: 2 per leaf, up to 6 per growing tip. Average Length: 7/16" [11.1 mm.]. Color: Brilliant yellow green [116. brill.YG] with a Moderate reddish brown [43. m.rBr] tinge around the edges.
*Glands.*—Number: 2 to 4. Position: Alternately and oppositely positioned on the petiole and base of blade. Size: Small. Form: Globose. Color: Light yellow green [119. l.YG].
*Leaf buds.*—Pointed.
Flower buds:
*Hardiness.*—Hardy, with respect to central California winters.
*Diameter.*—Typically 3/16" [4.8 mm.] 1 week before bloom.
*Length.*—Typically ⅜" [9.5 mm.] 1 week before bloom.
*Form.*—Not appressed.
*Surface.*—Smooth, not pubescent.
*Color.*—White [263. White].
Flowers: Perfect, complete, perigynous, usually a single pistil, typically twenty-four or more stamens, five sepals and petal locations alternately positioned.
*Average flower diameter.*—¾" [19.1 mm.].
*Number of petals.*—Five, no double blossoms observed.
*Petal shape.*—Oval.
*Petal margin.*—Slightly wavy.
*Average petal diameter.*—¼" [6.4 mm.].
*Average petal length.*—⅜" [9.5 mm.].
*Petal apex.*—Rounded.
*Petal base.*—Rounded to slightly cordate.
*Petal color.*—White [263. White].
*Anther color.*—Brilliant orange yellow [67. brill.OY].
*Stigma color.*—Light greenish yellow [101. l.gY].
*Sepal color.*—Light yellow green [119. l.YG].
*Sepal length.*—5/32" [4 mm.].
*Sepal width.*—⅛" [3 mm.].
*Average pistil length.*—5/16" [7.9 mm.].
*Average stamen length.*—⅜" [9.5 mm.].
*Fragrance.*—Moderate when nectar is present.
*Blooming period.*—Medium compared with other varieties.
*Onset of bloom*—One percent on Feb. 24, 2001.
*Date of full bloom.*—Mar. 10, 2001.
*Duration of bloom.*—One to two weeks, dependent on ambient temperature.
*Number per cluster.*—Average 5, rarely less than 2 or more than 9.

FRUIT

Maturity when described: Firm ripe, Jun. 27, 2001.
Date of first picking: Jun. 24, 2001.
Date of last picking: Jul. 2, 2001.
Size: Uniform, medium.
*Average diameter axially.*—2 5/16" [58.7 mm.].
*Average diameter across suture plane.*—2 7/16" [61.9 mm.].
*Typical weight.*—4.9 ounces [139 grams].
Form: Uniform, symmetrical, globose, some slightly compressed axially.
*Longitudinal section form.*—Roundish to elliptical.
*Transverse section through diameter.*—Round.
Suture: An inconspicuous line from the apex to the stem.
Ventral surface: Rounded.
Lips: None.
Cavity: Flaring, circular, suture showing on one side.
*Depth.*—⅜" [9.5 mm.].
*Breadth.*—¾" [19.1 mm.].
Base: Truncate.
Apex: Rounded, with a slight mammiform protrusion.
Pistil point: An inconspicuous dot located on the protrusion.
Stem: Small to medium.
*Average length.*—7/16" [11.1 mm.].
*Average width.*—3/32" [2.4 mm.].
Skin:
*Thickness.*—Medium.
*Surface.*—Smooth.
*Tenacity.*—Tenacious to flesh.
*Astringency.*—Slightly astringent.
*Tendency to crack.*—Slight in wet season.
*Color.*—Very dark red [17. v.d.R] to Deep reddish brown [41. deep rBr] with moderate Light orange yellow [70. l.OY] freckling and occasional Light yellow green [119. l.YG] areas where completely sun protected.

*Bloom.*—Abundant.

Flesh:

*Color.*—Light yellow [86. l.Y] toward the stone with substantial Deep red [13. deep R] bleeding next to the skin increasing with maturity.

*Surface of pit cavity.*—Light yellow [86. l.Y] fibers breaking when twisted from the stone.

*Amygdalin.*—Scarce.

*Juice.*—Very abundant, rich.

*Texture.*—Firm.

*Fibers.*—Abundant, fine.

*Ripens.*—Earlier toward the apex.

*Flavor.*—Very sweet with only moderate acid, 16 to 18 brix, no tartness toward the stone.

*Aroma.*—Moderate.

*Eating quality.*—Excellent.

STONE

Type: Clingstone.
Form: Oval.
Hilum: Narrow.
Base: Somewhat oblique.
Apex: Rounded, with a very sharply protruding tip 3/32" [2.4 mm.] long.
Sides: Equal.
Surface: Somewhat rough with a few vertical ridges.
Ridges: Somewhat sharp, less than 1/32" [0.8 mm.] in height.
Color: Light orange yellow [70. l.OY].
Average pit wall thickness: 1/16" [1.6 mm.].
Average width: 5/8" [15.9 mm.].
Average length: 15/16" [23.8 mm.].
Average breadth: 3/8" [9.5 mm.].
Tendency to split: Very slight.

Kernel:

*Form.*—Oval.

*Pellicle color.*—Brownish orange [54. brO].

*Skin color.*—Pale yellow [89. p.Y] when first removed.

*Vein color.*—Brownish orange [54. brO].

*Taste.*—Very bitter.

*Viable.*—Yes.

*Average width.*—3/8" [9.5 mm.].

*Average length.*—1/2" [12.7 mm.].

*Amygdalin.*—Abundant.

USE

Market: Fresh market and long distance shipping.
Keeping quality: Good. Fruit quality observed to remain in good condition in after 14 days in standard cold room at 36° Fahrenheit [2° Celsius].
Shipping quality: Good.
Resistance to insects: No unusual susceptiblities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to 'Purple Majesty' (U.S. Plant Pat. No. 7,503), by producing dark red plums that are firm in texture and mature about the third week in June, but is distinguished therefrom and an improvement thereon by being self-fertile, by producing an abundance of pollen, by being more productive, and by producing fruit that is red in flesh color toward the skin, juicier, and sweeter in flavor.

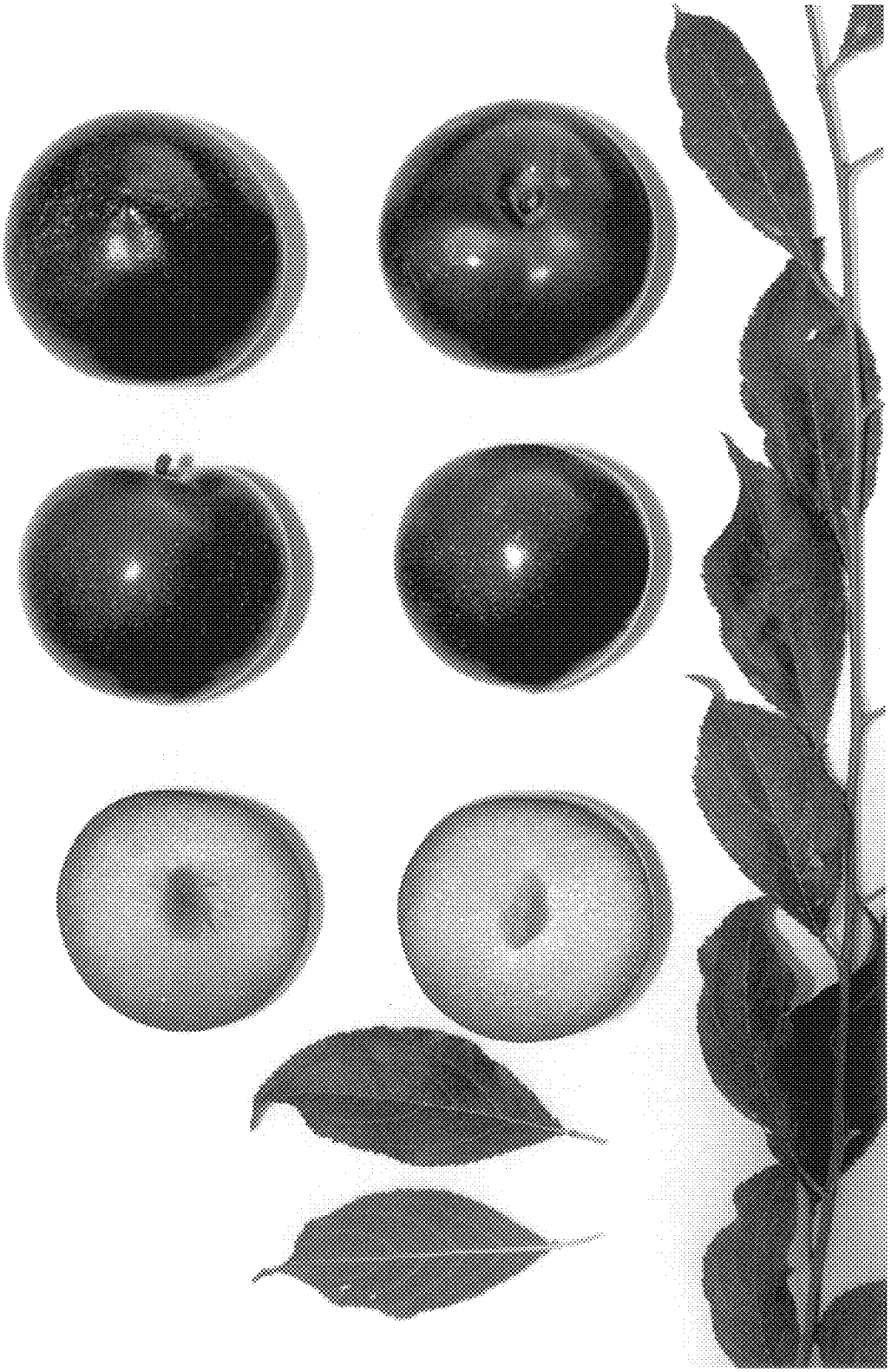

* * * * *